(12) United States Patent
Choi et al.

(10) Patent No.: US 12,167,923 B2
(45) Date of Patent: Dec. 17, 2024

(54) BACKSCATTERED X-RAY IMAGING DEVICE BASED ON MULTI-SOURCES

(71) Applicant: ELECTRONICS AND TELECOMMUNICATIONS RESEARCH INSTITUTE, Daejeon (KR)

(72) Inventors: Sunghoon Choi, Daejeon (KR); Yoon-Ho Song, Daejeon (KR); Jin-Woo Jeong, Daejeon (KR); Sora Park, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 247 days.

(21) Appl. No.: 17/861,841

(22) Filed: Jul. 11, 2022

(65) Prior Publication Data

US 2023/0078172 A1 Mar. 16, 2023

(30) Foreign Application Priority Data

Jul. 13, 2021 (KR) .................. 10-2021-0091735
Jun. 28, 2022 (KR) .................. 10-2022-0079016

(51) Int. Cl.
  *A61B 6/40* (2024.01)
  *A61B 6/04* (2006.01)
  *A61B 6/42* (2024.01)

(52) U.S. Cl.
  CPC .......... *A61B 6/4071* (2013.01); *A61B 6/0471* (2013.01); *A61B 6/4007* (2013.01); *A61B 6/4291* (2013.01)

(58) Field of Classification Search
  CPC ... A61B 6/4071; A61B 6/0471; A61B 6/4007; A61B 6/4291
  See application file for complete search history.

(56) References Cited

U.S. PATENT DOCUMENTS

| | | | | |
|---|---|---|---|---|
| 5,033,073 A * | 7/1991 | Friddell | ............... | G01N 23/203 378/146 |
| 5,260,982 A * | 11/1993 | Fujii | .................. | G01V 5/22 378/57 |
| 5,493,596 A * | 2/1996 | Annis | .................... | G21K 1/043 378/146 |
| 5,600,303 A * | 2/1997 | Husseiny | ............ | G01N 23/207 340/568.1 |

(Continued)

FOREIGN PATENT DOCUMENTS

| | | |
|---|---|---|
| JP | H6-138252 A | 5/1994 |
| JP | H8-247971 A | 9/1996 |
| JP | H9-33458 A | 2/1997 |

*Primary Examiner* — Hugh Maupin

(57) ABSTRACT

Provided is a backscattered X-ray image device based on multi-sources. The backscattered X-ray image device includes an X-ray tube array configured to generate X-rays, first slit plates provided on the X-ray tube array and having a first slit through which the X-rays pass, second slit plates provided on the first slit plates and having second slits defined in a direction different from that of the first slit, and detectors provided on the second slit plates and having a narrow gap in the same direction as the first slit, the detectors being configured to detect a backscattered beam that is emitted from a subject receiving the X-rays.

14 Claims, 4 Drawing Sheets

(56) References Cited

U.S. PATENT DOCUMENTS

| | | |
|---|---|---|
| 7,233,644 B1 | 6/2007 | Bendahan |
| 10,762,998 B2 | 9/2020 | Rothschild |
| 2005/0089140 A1* | 4/2005 | Mario ................. G01N 23/046 378/57 |
| 2006/0245548 A1* | 11/2006 | Callerame ............. G01V 5/222 378/57 |
| 2014/0161232 A1 | 6/2014 | Jeong |
| 2018/0247787 A1 | 8/2018 | Jeong |
| 2018/0294066 A1 | 10/2018 | Rothschild |
| 2020/0233100 A1* | 7/2020 | Rothschild ............ G01T 1/2018 |
| 2021/0074445 A1 | 3/2021 | Rothschild |
| 2023/0236141 A1* | 7/2023 | Bendahan ........ G01N 23/20008 378/87 |
| 2023/0290533 A1* | 9/2023 | Rothschild ............. G21K 1/043 |

\* cited by examiner

BACKSCATTERED X-RAY IMAGING DEVICE BASED ON MULTI-SOURCES

CROSS-REFERENCE TO RELATED APPLICATIONS

This U.S. non-provisional patent application claims priority under 35 U.S.C. § 119 of Korean Patent Application No. 10-2021-0091735, filed on Jul. 13, 2021, and 10-2022-0079016, filed on Jun. 28, 2022, the entire contents of which are hereby incorporated by reference.

BACKGROUND

The present disclosure herein relates to a backscattered X-ray image device, and more particularly, to a backscattered X-ray image device based on multi-sources.

In general, an X-ray backscatter image is an image that detects X-rays scattered at an angle of about 180 degrees by using a feature, in which the X-rays are scattered more than transmitted through a low-density organic material subject. The X-ray backscatter image using the above-described feature is widely used in fields of security screening to examine narcotics, psychoactive substances, and detonators made of plastic substances, which are difficult to be observed through X-ray transmission images. In the X-ray transmission image, a large area may be obtained at once because an attenuated X-ray signal is different after the transmission according to a density and thickness of the subject. On the other hand, in the X-ray backscatter image, there is a limitation that incident X-rays have to be as narrow as possible because a backscattered signal from a local area of the subject has not to affect signals of other local areas. The X-ray backscattered image may be acquired through an imaging device that is emitted in a pencil beam scanning mode.

SUMMARY

The present disclosure provides a backscattered X-ray imaging device capable of increasing in resolution of a pencil beam.

An embodiment of the inventive concept provides a backscattered X-ray imaging device. The backscattered X-ray image device includes: an X-ray tube array configured to generate X-rays; first slit plates provided on the X-ray tube array and having a first slit through which the X-rays pass; second slit plates provided on the first slit plates and having second slits defined in a direction different from that of the first slit; and detectors provided on the second slit plates and having a narrow gap in the same direction as the first slit, the detectors being configured to detect a backscattered beam that is emitted from a subject receiving the X-rays.

In an embodiment, the backscattered X-ray image device may further include a conveyor belt provided on the detectors and configured to allow the subject to move.

In an embodiment, the backscattered X-ray image device may further include a vibrator connected to the second slit plates and configured to vibrate the second slit plates.

In an embodiment, the first slit and the narrow gap may extend in a first direction, and In an embodiment, the vibrator may allow the second slits to move in the first direction.

In an embodiment, the second slits may extend in a second direction perpendicular to the first direction.

In an embodiment, the backscattered X-ray image device may further include lower rotating choppers provided between the X-ray tube array and the first slit plates.

In an embodiment, the backscattered X-ray image device may further include middle rotating choppers provided between the first slit plates and the second slit plates.

In an embodiment, the backscattered X-ray image device may further include upper rotating choppers provided between the second slit plates and the detectors.

In an embodiment, each of the lower rotating choppers, the middle rotating choppers, and the upper rotating choppers may include chopper slits.

In an embodiment, the chopper slits of the lower rotating choppers, the middle rotating choppers, and the upper rotating choppers may be aligned.

In an embodiment of the inventive concept, a backscattered X-ray image device includes: an X-ray tube array configured to generate X-rays; first slit plates provided on the X-ray tube array and having a first slit through which the X-rays pass; rotating choppers provided on the first slit plate to allow the X-rays to selectively pass therethrough so as to generate a pencil beam; detectors provided on the rotating choppers and configured to detect a backscattered beam that is emitted from a subject receiving the X-rays; and a conveyor belt provided on the detectors and configured to hold the subject.

In an embodiment, the backscattered X-ray image device may further include second slits provided between the detectors and the first slit plates and having second slits extending in a direction different from that of the first slit.

In an embodiment, the rotating choppers may include lower rotating choppers between the first slit plates and the second slit plates.

In an embodiment, the rotating choppers may further include middle rotating choppers between the second slit plates and the detectors.

In an embodiment, the rotating choppers may further include upper rotating choppers between the detectors and the conveyor belt.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
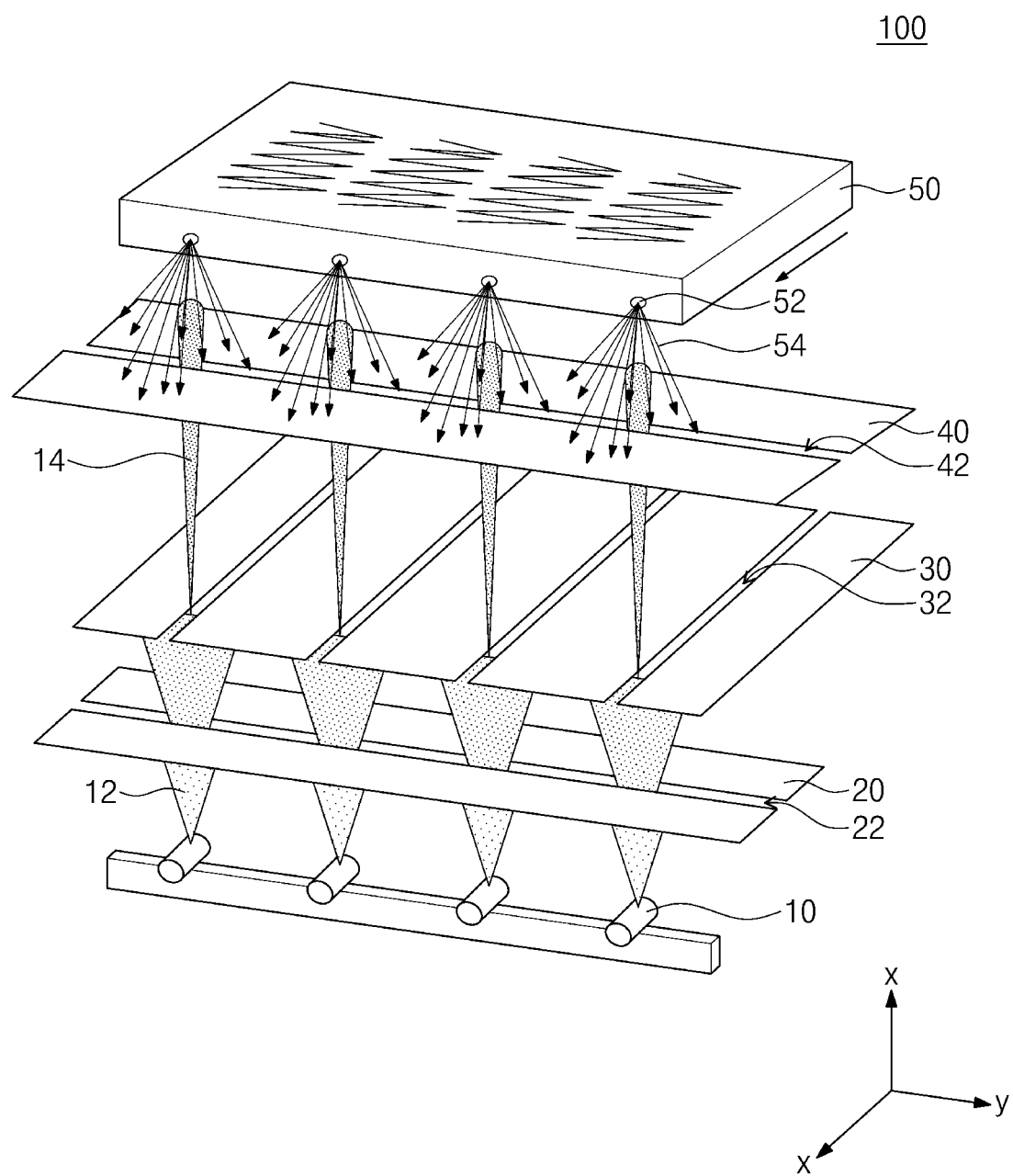
FIG. 1 is a view illustrating an example of a backscattered X-ray imaging device according to an embodiment of the inventive concept.

Preferred embodiments of the present invention will be described below in detail with reference to the accompanying drawings. Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art, and the present invention is only defined by the scope of the claims. Like reference numerals refer to like elements throughout.

In the following description, the technical terms are used only for explaining a specific exemplary embodiment while not limiting the present invention. In this specification, the terms of a singular form may comprise plural forms unless specifically mentioned. The meaning of 'comprises' and/or 'comprising' specifies a component, an operation and/or an element does not exclude other components, operations and/or elements. Since preferred embodiments are provided below, the order of the reference numerals given in the description is not limited thereto.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes.

FIG. 1 is a view illustrating an example of a backscattered X-ray imaging device according to an embodiment of the inventive concept.

Referring to FIG. 1, a backscattered X-ray imaging device 100 according to an embodiment of the inventive concept may include an X-ray tube array 10, first slit plates 20, second slit plates 30, detectors 40, and a conveyor belt 50.

The X-ray tube array 10 may provide X-rays 12 to the first slit plates 20, the second slit plates 30, the detectors 40, the conveyor belt 50, and a subject 52. The X-ray tube array 10 may include a plurality of X-ray tubes arranged in a second direction y. The plurality of X-ray tubes may be provided in about N number. Each of the plurality of X-ray tubes may generate the X-rays 12. The X-rays 12 may be provided to the first slit plates 20 in a cone shape or a bugle shape.

The first slit plates 20 may be provided on the X-ray tube array 10. The first slit plates 20 may be horizontal plates. The first slit plates 20 may have a first slit 22. The first slit 22 may extend in the second direction y. The first slit 22 may transmit and/or deform the X-rays 12 in a shape of a fan, a triangle, or an arc. The first slit plates 20 may be fixed to the X-ray tube array 10. The first slit plates 20 may include a metal or a polymer, but an embodiment of the inventive concept is not limited thereto.

The second slit plates 30 may be provided on the first slit plates 20. The second slit plates 30 may be vertical plates. The second slit plates 30 may extend in a direction perpendicular to the first slit plates 20. The second slit plates 30 may have second slits 32. The second slits 32 may be arranged in a direction crossing the first slit 22. The second slits 32 may extend in a first direction x. The second slits 32 may transmit a portion of the X-rays 12 to generate a pencil beam 14. The pencil beam 14 may be a point beam. The pencil beam 14 may be provided to the subject 52.

Thus, the backscattered X-ray imaging device 100 according to an embodiment of the inventive concept may increase in resolution of the pencil beam 14 by using the second slit plates 30 having the second slits 32. The X-ray tube array 10 may sequentially drive the X-ray tubes to eliminate a loss of a line area of the first slit 22 and a line area of the second slits 32. The X-ray tube array 10 may sequentially be turned on and turned off.

The detectors 40 may be provided on the second slit plates 30. Each of the detectors 40 may have a narrow gap 42 or an empty space. The pencil beam 14 may pass through the narrow gap 42 so as to be transmitted to the subject 52. The narrow gap 42 may have the same direction as that of the first slit 22. The narrow gap 42 may extend in the second direction y. The detectors 40 may detect the backscattered X-rays 54 generated from the subject 52. A controller (not shown) may acquire a backscattered image by using a detection signal of the backscattered X-ray 54 of the detectors 40.

A conveyor belt 50 may be provided on the detectors 40. The conveyor belt 50 may clamp or hold the subject 52 to allow the subject 52 to move in a direction of an arrow. The conveyor belt 50 may allow the subject 52 to move in the first direction x. Although not shown, the conveyor belt 50 may allow the subject 52 to move in the second direction y or a third direction z, but an embodiment of the inventive concept is not limited thereto.

Figure 2:
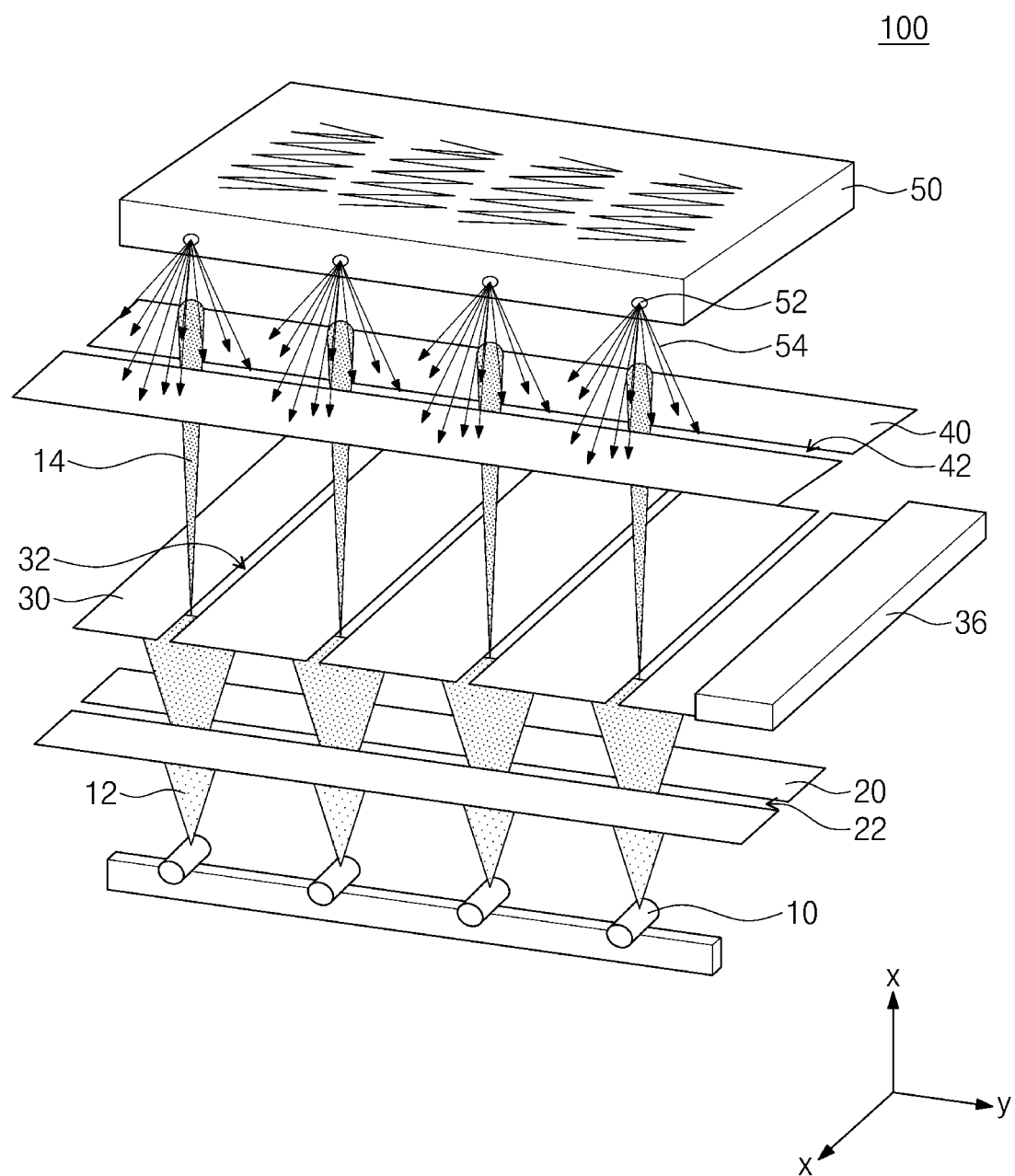
FIG. 2 is a view illustrating an example of the backscattered X-ray imaging device according to an embodiment of the inventive concept.

FIG. 2 is a view illustrating an example of the backscattered X-ray imaging device according to an embodiment of the inventive concept.

Referring to FIG. 2, the backscattered X-ray imaging device 100 according to an embodiment of the inventive concept may further include a vibrator 36. The X-ray tube array 10, the first slit plates 20, the detector 40, and the conveyor belt 50 may be configured in the same manner as in FIG. 1.

The vibrator 36 may be connected to one side of the second slit plates 30. The vibrator 36 may allow the second slit plates 30 to reciprocally and/or periodically move in the second direction y. The vibrator 36 may vibrate the second slit plates 30 to increase in resolution of the pencil beam 14. The vibrator 36 may include a deflection weight motor vibrator or an ultrasonic vibrator, but an embodiment of the inventive concept is not limited thereto.

The X-ray tube array 10 is sequentially driven from first to N-th tubes, and the vibrator 36 may allow the second slits 32 to move in synchronization with a driving speed of the X-ray tube array 10.

FIG. 2 is a view illustrating an example of the backscattered X-ray imaging device according to an embodiment of the inventive concept.

Figure 3:
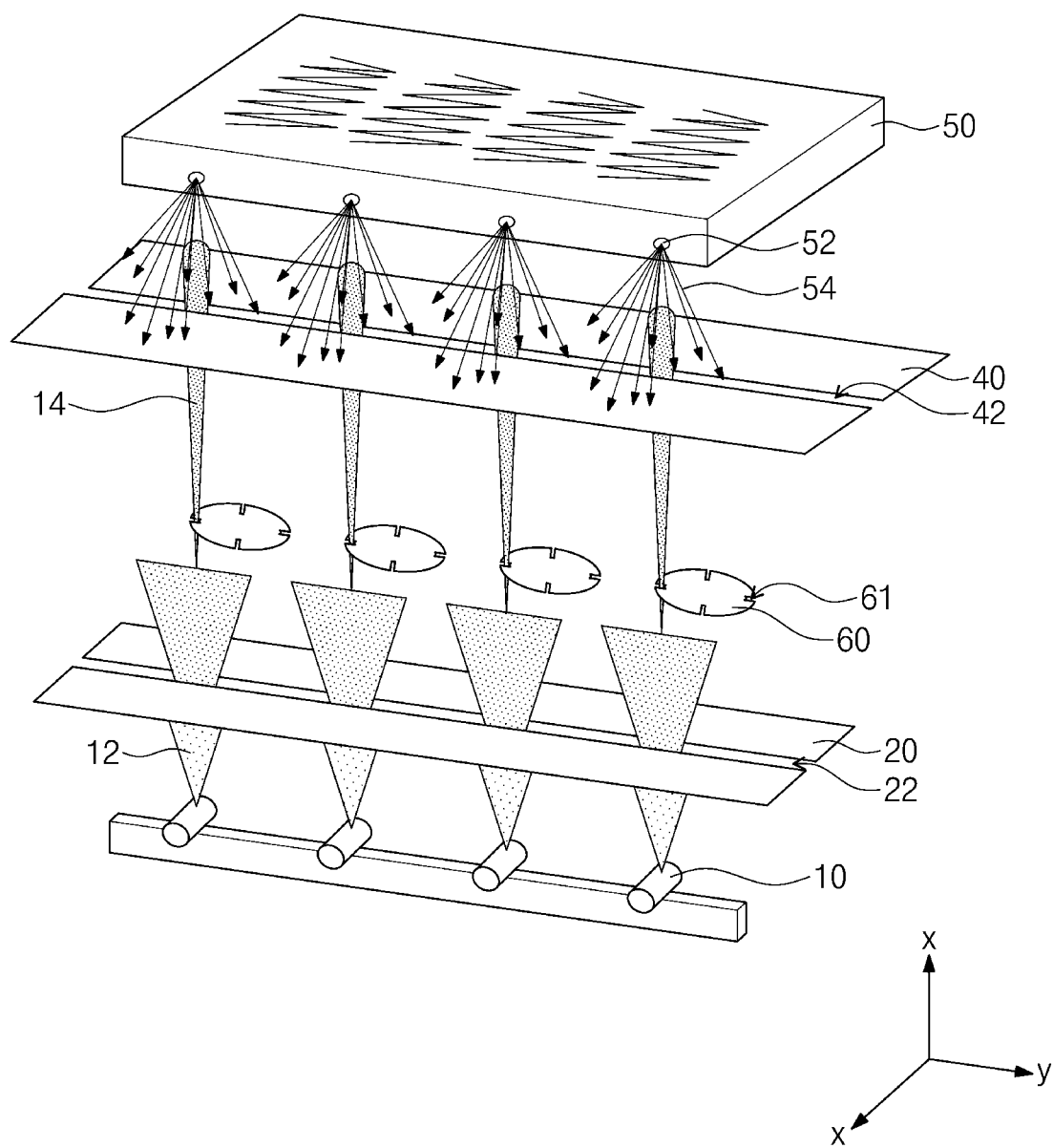
FIG. 3 is a view illustrating an example of the backscattered X-ray imaging device according to an embodiment of the inventive concept.

Referring to FIG. 3, the backscattered X-ray imaging device 100 according to an embodiment of the inventive concept may further include rotating choppers 60. The X-ray tube array 10, the first slit plates 20, the detector 40, and the conveyor belt 50 may be configured in the same manner as in FIG. 1.

The rotating choppers 60 may be provided between the first slit plates 20 and the detectors 40. The rotating choppers 60 may be replaced with the second slit plates 30 of FIGS. 1 and 2. The rotating choppers 60 may be aligned with the X-ray tubes of the X-ray tube array 10, respectively. That is, the rotating choppers 60 may individually correspond to the X-ray tubes. The rotating choppers 60 may have chopper slits 61 or apertures. The chopper slits 61 may allow the X-rays 12 to selectively pass therethrough so as to generate the pencil beam 14. The chopper slits 61 may provide the pencil beam 14 to the subject 52.

Thus, the backscattered X-ray imaging device 100 according to an embodiment of the inventive concept may increase in resolution of the pencil beam 14 by using the rotating choppers 60 having the chopper slits 61.

Figure 4:
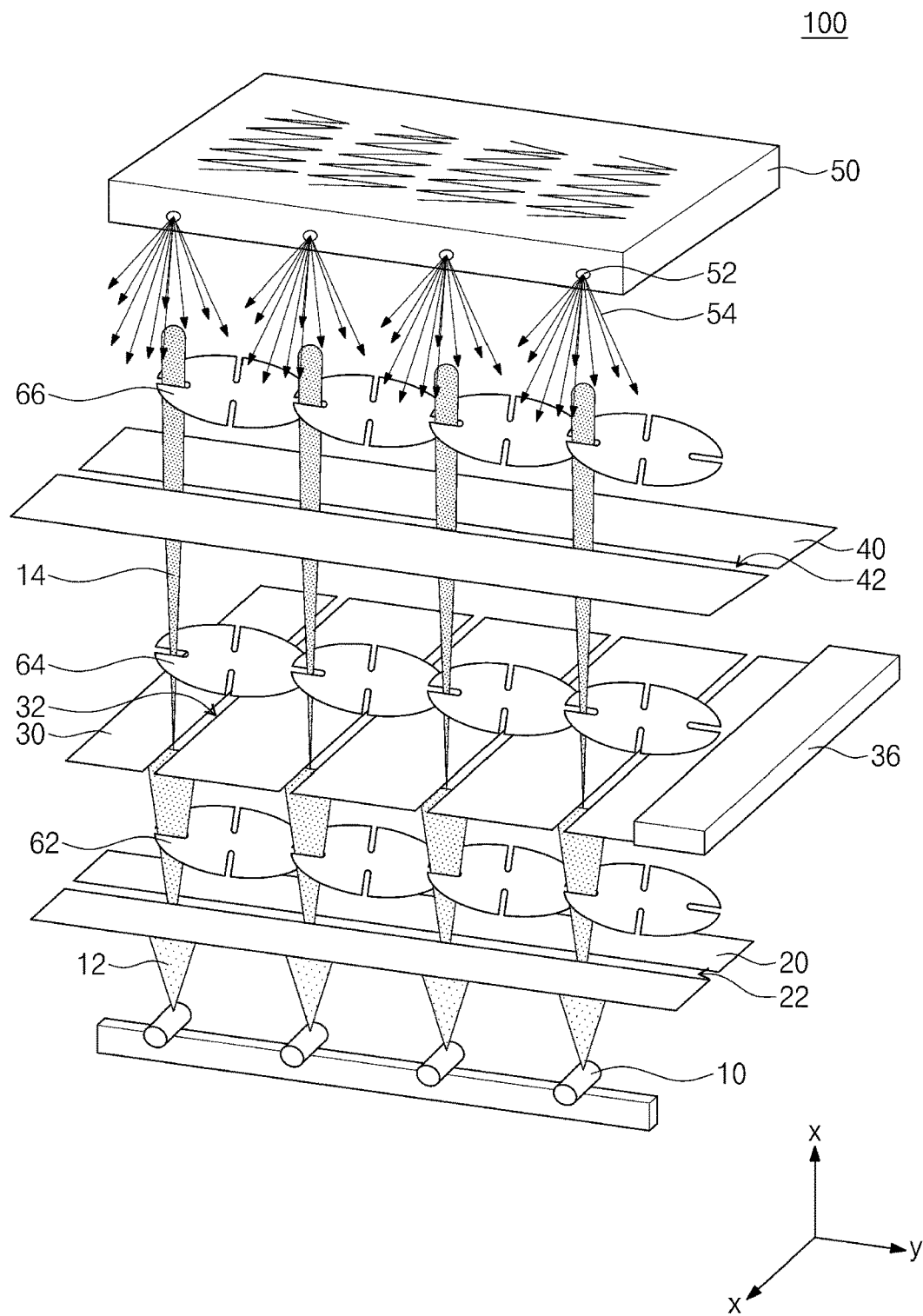
FIG. 4 is a view illustrating an example of the backscattered X-ray imaging device according to an embodiment of the inventive concept.

FIG. 4 is a view illustrating an example of the backscattered X-ray imaging device according to an embodiment of the inventive concept.

Referring to FIG. 4, the backscattered X-ray imaging device 100 according to an embodiment of the inventive concept may further include lower rotating choppers 62, middle rotating choppers 64, and upper rotating choppers 66. Each of the lower rotating choppers 62, the middle rotating choppers 64, and the upper rotating choppers 66 may have the chopper slits 61 of FIG. 3. The chopper slits 61 of the lower rotating choppers 62, the middle rotating choppers 64, and the upper rotating choppers 66 may be aligned in the third direction z. The X-ray tube array 10, the first slit plates 20, the second slit plates 30, the vibrator 36, the detector 40, and the conveyor belt 50 may be configured in the same manner as in FIG. 2.

The lower rotating choppers 62 may be provided between the first slit plates 20 and the second slit plates 30. The lower rotating choppers 62 may allow the X-rays 12 to selectively pass therethrough so as to generate the pencil beam 14.

The middle rotating choppers 64 may be provided on the lower rotating choppers 62. The middle rotating choppers 64 may be provided between the second slit plates 30 and the detectors 40. The middle rotating choppers 64 may allow the pencil beam 14 to selectively pass therethrough so as to increase in resolution of the pencil beam 14.

The upper rotating choppers 66 may be provided on the middle rotating choppers 64. The upper rotating choppers 66 may be provided between the detectors 40 and the conveyor belt 50. The upper rotating choppers 66 may allow the pencil beam 14 to selectively pass therethrough so as to improve the resolution of the pencil beam 14.

As described above, the resolution of the pencil beam may increase by using the first and second slit plates having first and second slits crossing each other according to the embodiment of the inventive concept.

Although the embodiment of the inventive concept is described with reference to the accompanying drawings, those with ordinary skill in the technical field of the inventive concept pertains will be understood that the present disclosure can be carried out in other specific forms without changing the technical idea or essential features. Thus, the above-disclosed embodiments are to be considered illustrative and not restrictive.

What is claimed is:

1. A backscattered X-ray image device comprising:
an X-ray tube array configured to generate X-rays;
first slit plates provided on the X-ray tube array and having a first slit through which the X-rays pass;
second slit plates provided on the first slit plates and having second slits defined in a direction different from that of the first slit;
a vibrator connected to the second slit plates and configured to vibrate the second slit plates; and
detectors provided on the second slit plates and having a narrow gap in the same direction as the first slit, the detectors being configured to detect a backscattered beam that is emitted from a subject receiving the X-rays.

2. The backscattered X-ray image device of claim 1, further comprising a conveyor belt provided on the detectors and configured to allow the subject to move.

3. The backscattered X-ray image device of claim 1, wherein the first slit and the narrow gap extend in a first direction, and the vibrator allows the second slits to move in the first direction.

4. The backscattered X-ray image device of claim 3, wherein the second slits extend in a second direction perpendicular to the first direction.

5. The backscattered X-ray image device of claim 1, further comprising lower rotating choppers provided between the X-ray tube array and the first slit plates.

6. The backscattered X-ray image device of claim 5, further comprising middle rotating choppers provided between the first slit plates and the second slit plates.

7. The backscattered X-ray image device of claim 6, further comprising upper rotating choppers provided between the second slit plates and the detectors.

8. The backscattered X-ray image device of claim 7, wherein each of the lower rotating choppers, the middle rotating choppers, and the upper rotating choppers comprises chopper slits.

9. The backscattered X-ray image device of claim 8, wherein the chopper slits of the lower rotating choppers, the middle rotating choppers, and the upper rotating choppers are aligned.

10. A backscattered X-ray image device comprising:
an X-ray tube array configured to generate X-rays;
first slit plates provided on the X-ray tube array and having a first slit through which the X-rays pass;
rotating choppers provided on the first slit plate to allow the X-rays to selectively pass therethrough so as to generate a pencil beam;
detectors provided on the rotating choppers and configured to detect a backscattered beam that is emitted from a subject receiving the X-rays;
second slit plates provided between the detectors and the first slit plates and having second slits extending in a direction different from that of the first slit; and
a conveyor belt provided on the detectors and configured to hold the subject,
wherein the rotating choppers comprise lower rotating choppers between the first slit plates and the second slit plates.

11. The backscattered X-ray image device of claim 10, wherein the rotating choppers further comprise middle rotating choppers between the second slit plates and the detectors.

12. The backscattered X-ray image device of claim 11, wherein the rotating choppers further comprise upper rotating choppers between the detectors and the conveyor belt.

13. A backscattered X-ray image device comprising:
an X-ray tube array configured to generate X-rays;
first slit plates provided on the X-ray tube array and having a first slit through which the X-rays pass;
second slit plates provided on the first slit plates and having second slits defined in a direction different from that of the first slit;
middle rotating choppers provided between the first slit plates and the second slit plates; and
detectors provided on the second slit plates and having a narrow gap in the same direction as the first slit, the detectors being configured to detect a backscattered beam that is emitted from a subject receiving the X-rays.

14. The backscattered X-ray image device of claim 13, further comprising lower rotating choppers provided between the X-ray tube array and the first slit plates.

* * * * *